United States Patent [19]
Augenblick et al.

[11] Patent Number: 5,363,707
[45] Date of Patent: Nov. 15, 1994

[54] HEADSPACE SAMPLING SYSTEM

[75] Inventors: Kurt B. Augenblick, Wilmington, Del.; Paul B. Crilly, Knoxville, Tenn.; Steven J. Engel, Kennett Square, Pa.; Kimber D. Fogelman, Hockessin, Del.

[73] Assignee: Hewlett-Packard Company, Palo Alto, Calif.

[21] Appl. No.: 877,909

[22] Filed: May 1, 1992

[51] Int. Cl.$^5$ ............................................. G01N 1/22
[52] U.S. Cl. ........................... 73/864.84; 73/863.81; 73/863.86; 73/864.21; 73/864.83; 73/864.87
[58] Field of Search ......... 73/864.21–864.23, 73/864.81, 864.83, 864.84, 864.85, 864.87, 863.73, 863.86, 863.85, 863.81

[56] References Cited

U.S. PATENT DOCUMENTS

| | | | |
|---|---|---|---|
| 3,203,248 | 8/1965 | Stutler et al. | 73/863.85 |
| 3,374,678 | 3/1968 | McGuckin | 73/863.85 |
| 3,550,453 | 3/1969 | Lightner et al. | 73/864.21 |
| 3,849,070 | 11/1974 | Garza et al. | 73/864.74 |
| 4,003,257 | 1/1977 | Fletcher et al. | 73/23.1 |
| 4,096,734 | 6/1978 | Khayat | 73/863.81 |
| 4,199,988 | 4/1980 | Riegger | 73/863.81 |
| 4,268,478 | 5/1981 | Huber | 422/68 |
| 4,359,891 | 11/1981 | Ahlstrom, Jr. et al. | 73/23.1 |
| 4,376,391 | 3/1983 | Brunnee | 73/863.12 |
| 4,411,156 | 10/1983 | Lowe | 73/863.81 |
| 4,464,940 | 8/1984 | Pospisil | 73/864.21 |
| 4,467,038 | 8/1984 | Scott | 436/115 |
| 4,474,889 | 10/1984 | Terry et al. | 436/161 |
| 4,715,216 | 12/1987 | Muller | 73/61.1 |
| 4,786,736 | 11/1988 | Bronstert | 548/369 |
| 4,799,394 | 1/1989 | Barnett et al. | 73/864.81 |
| 4,872,992 | 10/1989 | Oquendo et al. | 210/659 |
| 4,951,512 | 8/1990 | Mazza et al. | 73/864.23 |

FOREIGN PATENT DOCUMENTS

| | | | |
|---|---|---|---|
| 2040695 | 1/1971 | France. | |
| 2907558 | 8/1980 | Germany | 73/863.85 |
| 0798529 | 1/9181 | U.S.S.R. | 73/863.85 |
| 9119181 | 12/1991 | WIPO | 73/863.85 |

OTHER PUBLICATIONS

R. E. Hurst, "Devices for sampling headspace from canned food", in Analytical Chemistry, vol. 47, No. 7, pp. 1221–1223, Jun. 1975.

J. Zielinski, "Microsampling valves of new design and their application: generation of concentration-programmed gaseous streams," *J. Phys. E. Sci. Instrum.*, vol. 16, pp. 24–25 (1983).

Primary Examiner—Hezron E. Williams
Assistant Examiner—George W. Dombroske
Attorney, Agent, or Firm—Richard Schuette

[57] ABSTRACT

Methods and apparatus for collecting gasses from the sample headspace of a sealed sample container are disclosed. The gasses in the sample headspace are withdrawn by inserting a probe into the sample headspace and permitting the gasses to flow into an external headspace. The probe is then disconnected from the sample to seal the external headspace and the external headspace is then connected to an analytical instrument such as a gas chromatograph to permit the sample gasses to be transferred out of the external headspace and into the instrument. The step of transferring the gasses is preferably accomplished by connecting a source of carrier gas to an inlet port of the external headspace and sweeping the sample gasses from the external headspace. In certain preferred embodiments of the present invention, vibration is used to promote the formation of sample gasses either by vibrating the sample container itself or by moving the sample container relative to a stop to vibrate a septum which seals the sample container in certain embodiments. In these embodiments, the agitation created by such vibrations increases the rate of outgassing from the sample to the sample headspace. Also, in certain embodiments, the external headspace includes a flexible portion that is vibrated to agitate the external headspace and thereby promote uniform dispersion of sample gasses throughout the headspace.

24 Claims, 3 Drawing Sheets

HEADSPACE SAMPLING SYSTEM

The present invention relates to gas chromatography and, more specifically, to methods and apparatus for withdrawing a sample of gas from a sample container.

BACKGROUND OF THE INVENTION

Gas chromatography is an analytical technique for both qualitative and quantitative analysis of solid, liquid and gaseous mixtures. This technique is important in both laboratory and industrial settings since it permits the components present in a sample to be analyzed. There are numerous ways in which samples for chromatographic analysis may be obtained. One technique, known as headspace sampling, provides gaseous phase samples from either liquids or solids that are sealed in a sample container. Typically, the sample container that holds the samples is hermetically sealed inside a chamber and heated or cooled to a predetermined temperature. Under suitable conditions, material contained or dissolved in the sample will form a gaseous phase sample. As used herein, the term "headspace" refers to that portion of the sealed sample container that is not occupied by the solid or liquid sample, however, the headspace may be occupied by other gasses that are displaced or mixed with the sample gasses after equilibration of the sample begins. Thus, for one example, if carbonated water in a sealed container is heated, carbon dioxide will leave the water and occupy the headspace above the liquid remaining in the partially filled container. However, in certain instances where the sample container is completely filled, the "headspace" will exist in a closed region outside the sample container.

Components of the headspace sample gasses are in dynamic equilibrium with solid and/or liquid phase of the sample remaining in the container. That is to say that molecules of each gaseous component are continuously redissolved at the same rate as identical molecules are volatilized from the sample. This equilibrium is maintained only if the concentration of headspace components, as well as other conditions such as temperature and pressure, remain constant. In standard techniques, a portion of the equilibrated headspace is removed, thereby reducing the concentration of volatilized components and disturbing the equilibrium. The effect is that while the headspace region is being sampled, additional volatile components may enter the region. Since not all components of the sample volatilize at the same rate, the collected sample will be enriched with certain more volatile components and the analysis will yield incorrect results. This is undesirable, since the goal of headspace sampling is to remove an aliquot of sample without disturbing the relative concentrations of the various components.

In prior art headspace sampling systems the sample vessels are typically sealed by a diaphragm or septum, although other types of seals are also known. A probe pierces the septum to provide a flow of sample gas from the sample headspace to the entrance of a separating column of gas chromatograph, the flow of sample gas being controlled by a valve. The entrance to the separating column is also connected via a valve to a source of carrier gas. For example, in the system disclosed in U.S. Pat. No. 4,464,940—Pospisil the carrier gas is first pumped into the headspace to create an increased pressure, a valve disconnects the carrier gas and connects the probe with the separating column, thereby allowing carrier gas plus sample vapor to flow into the separating column, i.e., from a higher pressure to a lower pressure. However, in this and other headspace techniques currently in use, the headspace is significantly disturbed—by the increased pressure caused by direct introduction of a carrier gas or otherwise—and therefore, as explained above, the sample injected into the separating column is not exactly the same as that which existed in the undisturbed headspace. The disturbance or distortion of the headspace occurs either during pressurization of the sample container or upon withdrawal through the probe piercing the septum.

Conventional headspace techniques therefore rely upon the headspace sample equilibrating at a relatively high pressure then being sampled by expanding into a sample loop or directly into the head of a column. In either case, the actual headspace gasses are diluted by expansion to a larger volume. It would therefore be desirable to provide a headspace sample at lower or equal pressure to the inlet of an analytical instrument. In such a system no expansion would occur in the process of isolating the gaseous headspace sample from the original sample.

It would also be desirable to sample gaseous phase samples from the headspace of a sealed sample container without distorting or disturbing the composition of the gasses from the sample. Thus, it is an object of the present invention to provide methods and apparatus for transferring a gaseous sample from a sealed sample container to an analytical instrument without injecting a carrier gas into the sample container.

SUMMARY OF THE INVENTION

Accordingly, it has now been found that gasses in a sample container can be transferred to an analytical instrument by providing an external headspace that may be selectively connected to the sample container and then disconnected and isolated to permit the gasses that have been transferred into the external headspace to be transferred to an analytical instrument such as a gas chromatograph.

The present invention provides apparatus for collecting gasses from a sample contained in a sealed sample container that comprises an external headspace that is selectively connectable with the sample container. In certain embodiments a probe may be provided that connects the sample container to the external headspace in a sealed manner and in those embodiments where a septum is pierced by the probe, a shuttle valve preferably controls the flow of gasses through the probe. In such embodiments the shuttle valve is preferably disposed coaxially with the probe and adapted to be moved along the axial portion of the probe by the motion of the sample container. Thus, when the probe pierces the sample container, gas is permitted to flow from the sample container through the probe and into the external headspace. When the sample is removed, the shuttle valve acts to seal the probe and prevent the escape of gasses from the external headspace.

The present invention also includes a means for isolating the external headspace from the sample container. This may be accomplished, for example, by a switching valve provided for transferring the gaseous sample from the external headspace to an outlet port provided for this purpose. In a preferred embodiment of the present invention, the outlet port is connected to a gas chromatograph. Preferably, the switching valve is also connected to a source of carrier gas and to an inlet port provided on the external headspace so that when the switching valve is correctly positioned, carrier gas flows through the inlet port and sweeps the gasses contained in the external headspace through the outlet port and into an analytical instrument. In certain preferred embodiments of the present invention, the shape of the external headspace is optimized by providing a curved hollow portion which extends between the inlet port and the outlet port and also permits gas flow from the probe into the curved external headspace.

In certain embodiments of the present invention, improved transfer of gaseous constituents from the sample can be accelerated by vibrating and/or agitating the sample. Thus, certain embodiments of the present invention provide an ultrasonic vibrator for inducing localized ultrasonic vibrations in the sample container. Additionally, the time required for the gaseous sample to disperse throughout the headspace can be reduced by providing the external headspace with a flexible portion and a vibrator for vibrating this flexible portion to agitate the gasses in the sample headspace by agitating the external headspace. In another embodiment of the present invention, a stop is provided which urges against the septum or other seal and a vibrating means is provided to induce vibration between the sample container and the stop, thus agitating the gasses in the headspace by the motion of the septum or other sealing means.

In any of these embodiments, the apparatus of the present invention also preferably further comprises apparatus for creating one or more temperature controlled zones within the apparatus.

The present invention also discloses methods for collecting gasses from the headspace of a sample contained in a sample container. First, a substantially constant volume external headspace is connected to a sample container, and gasses contained in the sample container are permitted to flow into the external headspace. The external headspace is then isolated from the sample container and the gasses within the external headspace are transferred. In a preferred embodiment, the methods comprise the steps of inserting a probe into the sample container in a sealed manner and opening a valve to connect the sample headspace to an external headspace. Sample gasses are then permitted to flow from the sample headspace into the external headspace. The valve is then closed and a switching valve is opened to connect the external headspace to an outlet port thereby permitting the transfer of gasses from within the external headspace to an analytical instrument.

DETAILED DESCRIPTION OF THE PREFERRED EMBODIMENTS

Figure 1:
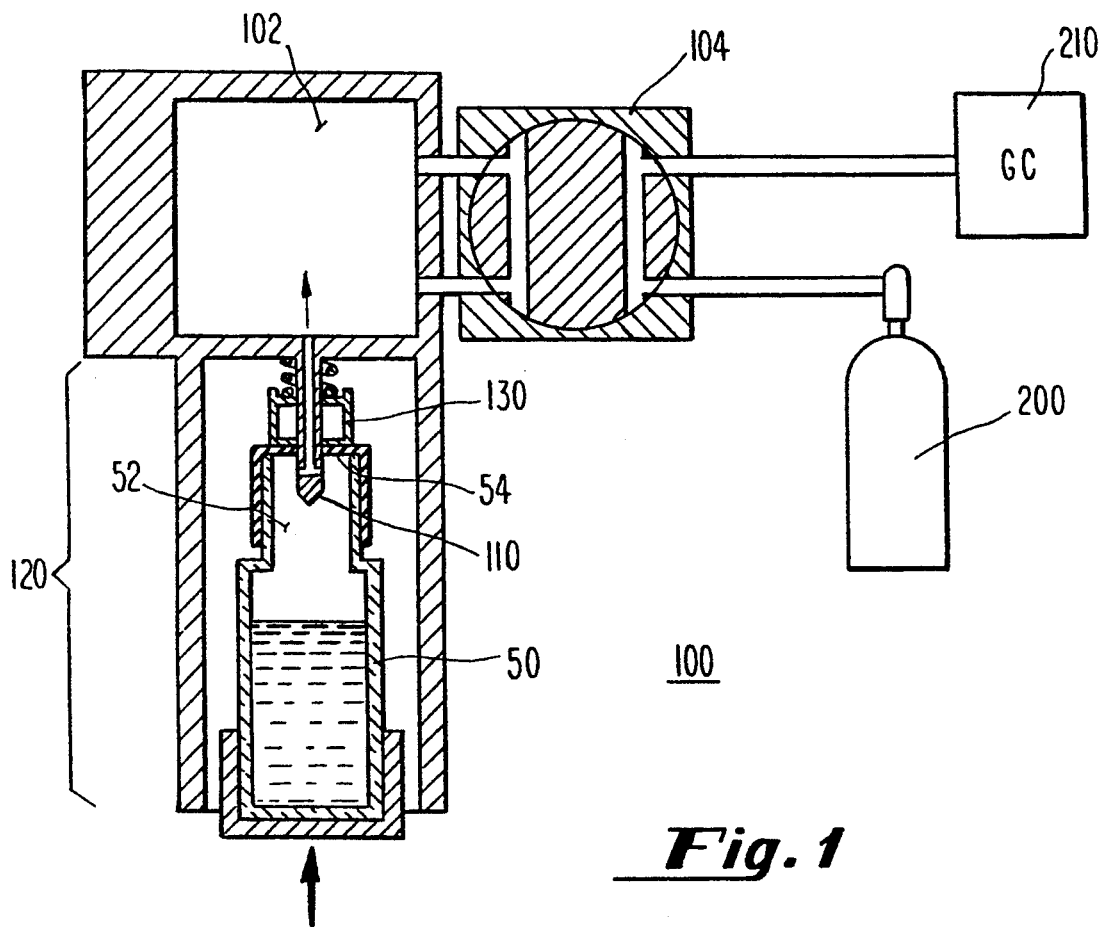
FIG. 1 is a partial cross-sectional elevation view of the headspace sampling apparatus of the present invention illustrating the withdrawal of a gaseous sample.

Referring now to FIG. 1, there is illustrated an external headspace device 100 that enables the gasses in the headspace 52 of a sample container 50 to be withdrawn and injected into an analytical instrument such as a gas chromatograph 210 without significant disturbance to its composition. FIG. 1 illustrates the apparatus 100 during the step of inserting the probe 110 through the septum 54 or other sealing means that seals the sample container 50, and into the sample headspace 52. In other embodiments sample containers other than those sealed using a septum may be employed, thus, means other the probe 110 described will be provided to permit sample gas to be released from the sample container. As shown by the arrow, the entire sample container 50 is preferably moved upward into a temperature controlled zone 120 until the probe 110 has pierced the septum 54 and the sample container 50 has also engaged and opened a shuttle valve 130, the operation of which is explained in further detail below. The construction and operation of the temperature controlled zone 120 will depend upon the volatility of the gasses in the sample and other factors. The determination of the parameters of the temperature controlled zone 120, as well as its construction and operation, are well known to those of ordinary skill in the art.

Figure 2:
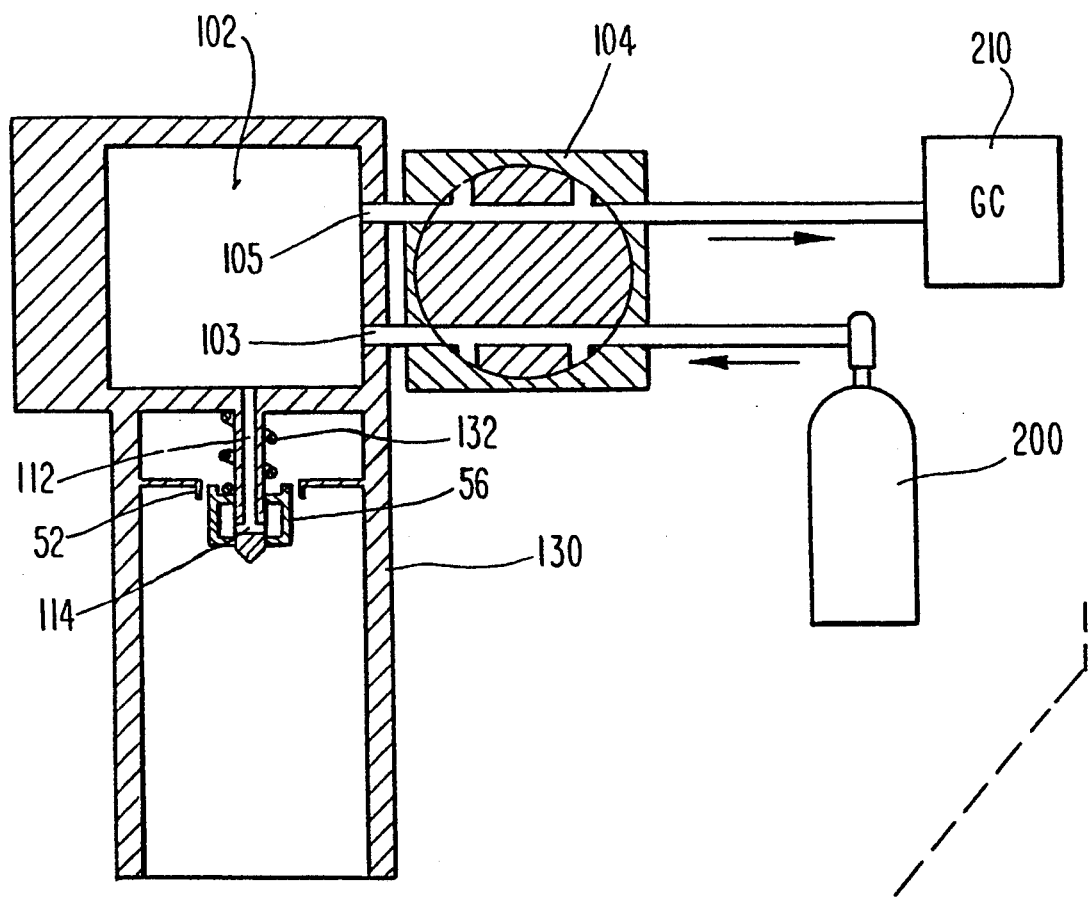
FIG. 2 is a view similar to FIG. 1, illustrating the evacuation of the external headspace made in accordance with the present invention.

In a preferred embodiment of the present invention, an external headspace 102 is directly connected to the sample headspace 52 by the probe 110. The passage of the gasses from the sample headspace 52 into the external headspace 102 is most preferably regulated by a shuttle valve 130. The shuttle valve 130 is most preferably constructed such that when the sample container 50 is urged upwardly into the probe 110, the same upward motion displaces the shuttle valve 130 and admits the gasses in the headspace 52 through the probe and into the external headspace 102. The shuttle valve 130 is thus preferably coaxially disposed around the probe 110. As seen by comparing FIG. 1 and FIG. 2, the shuttle valve 130 is moved along a portion of the axial length of the probe 110 by engagement with the sample container 50. Preferably, a spring 132, visible in FIG. 2, biases the shuttle valve 130 against the motion of the sample container 50. As also shown in FIG. 2, the probe 110 is preferably constructed to have an axial hollow portion 110 extending from the proximal end, near the external headspace 102, to a point near the distal end that is less than its overall length. The axial hollow portion 112 is thus a blind hole. However, in a preferred embodiment, a side passage 114 is disposed substantially perpendicular to the axial hollow portion 112. As seen in FIG. 1, when the sample container 50 moves the shuttle valve 130 along the axial length of the probe 110, the side passage 114 is opened and permits gasses to flow between the sample headspace 52 and the external headspace 102 via the probe 110. As shown in FIG. 2, when the sample container is removed, the shuttle valve 130 covers the side passage 114, effectively sealing the flow of gas through the probe 110 into or out of the external headspace 102. In other embodiments, the shuttle valve 130 can be replaced by other types of valves and piping junctions while still achieving the same effect.

The external headspace 102 is most preferably also temperature controlled to the same temperature as the temperature controlled zone 120 surrounding the sample container 50. Thus, upon the puncturing of the septum 52 by the probe 110 and opening of the shuttle valve 130, the gasses in the headspace 52 flow into the external headspace 102 until equilibrium is reached. The flow of gasses from the external headspace 102 is preferably regulated by the position of the four port switching valve 104 that is preferably disposed between the external headspace sampling device 100 of the present invention and a source of carrier gas 200 and a gas chromatograph 210 or other analytical instrument. Of course, as readily understood by those of ordinary skill, there are numerous other types of valves and piping arrangements that can be used in place of the four port switching valve 104 to effect the same flow path and achieve the same result.

The transfer of the sample gasses from the sample headspace 52 is illustrated in FIG. 2. As shown, the sample container 50 has been lowered from engagement with the probe 110 and shuttle valve 130, i.e., it is withdrawn from the temperature controlled zone 120. As explained above, the disengagement of the sample container 50 from the shuttle valve 130 results in the probe 110 being sealed to prevent the escape of the sample gasses within the external headspace 102. After the sample container 50 has been removed, the four port switching valve 104 is switched to an injection position. As shown by the arrows in FIG. 2, in the injection position the source of carrier gas 200 is connected to the external headspace 102 at an inlet port 103, permitting carrier gas to flow into the external headspace 102 and mix with the sample gasses therein. Another port on the switching valve 104 provides a connection between the external headspace 102 and a gas chromatograph 210 or other analytical instrument at an outlet port 105. Thus, carrier gas flows into the external headspace 102 and sweeps the sample gasses therein out of the external headspace and into the gas chromatograph 210 or other instrument. It will be appreciated that the operation of the present invention thus permits the gasses from a sample to be transferred from the sample container 50 to an analytical instrument such as a gas chromatograph 210 without significant disturbance, e.g., undue pressurization, within the sample container 50.

Figure 3:
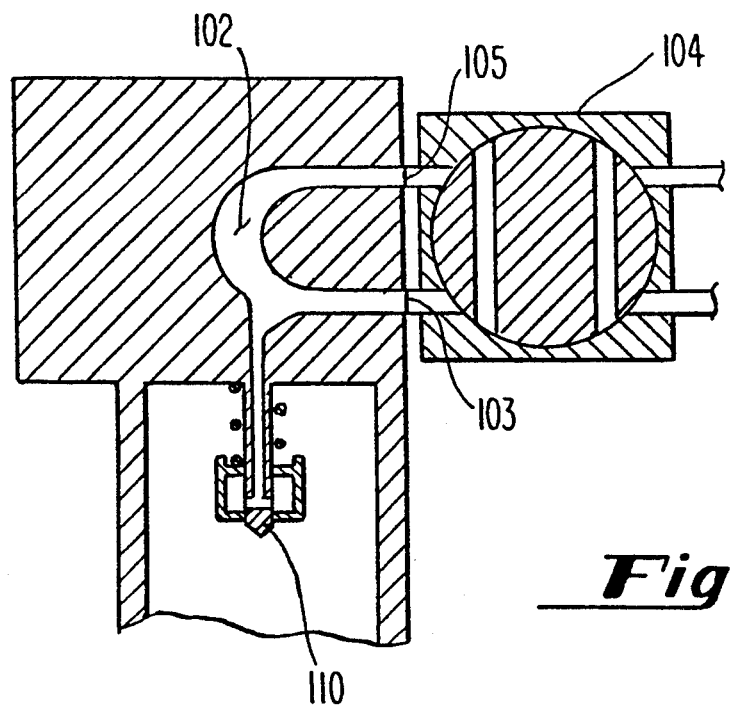
FIG. 3 illustrates an alternate embodiment of the external headspace of the present invention.

Referring now to FIG. 3, there is illustrated a view similar to that of FIG. 2 except that an alternate form of the external headspace 102 is shown. In this embodiment, the external headspace 102 has a curved shape between the inlet port 103 for the carrier gas and the outlet port 105 connecting the external headspace 102 to the four port switching valve 104. The curved portion also intersects the probe 110 to permit admission of gasses from the sample headspace 52 during the transfer step illustrated in FIG. 1 and discussed above. In this embodiment, the external headspace 102 is essentially in a form that eliminates unswept areas and creates a vortex that causes substantially all the gasses in the external headspace chamber 102 to be efficiently swept into the gas chromatograph 210. As will be readily appreciated by those of ordinary skill, a "curved" shape may be a toroidal or other annular segment and may describe either an arc segment or a hyperbola or other shape. The design and construction of a curved external headspace requires consideration of both the nature of the sample gasses and the pressure and flow rate of the carrier gas, along with other factors as would be realized by those of ordinary skill.

Thus, the embodiments of the present invention illustrated in FIGS. 1–3 provide a system for creating a gaseous sample without pressurizing the sample container 50. The sample headspace 52 within the sample container 50 is not unduly disturbed or diluted. The system of the present invention is thus inherently more sensitive than those found in the prior art. Additionally, the system of the present invention injects a constant volume of sample gas into a chromatograph or other instrument, creating results that are more reproducible than the headspace sampling methods used in the prior art.

Figure 5:
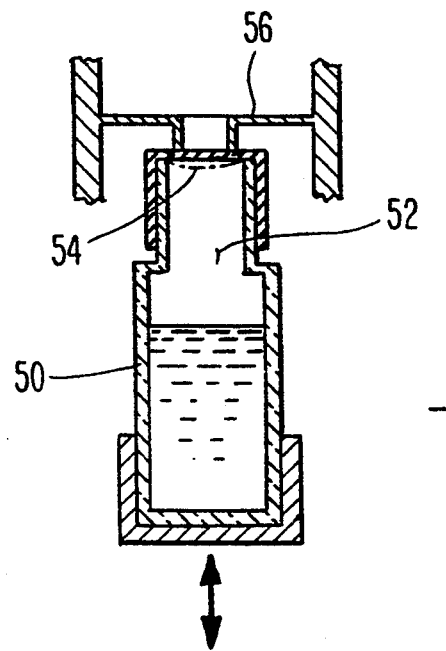
FIG. 5 illustrates an alternate embodiment of a portion of the headspace sampling apparatus of the present invention depicting agitation of the sample headspace to accelerate the formation of gasses from the sample.
Figure 4:
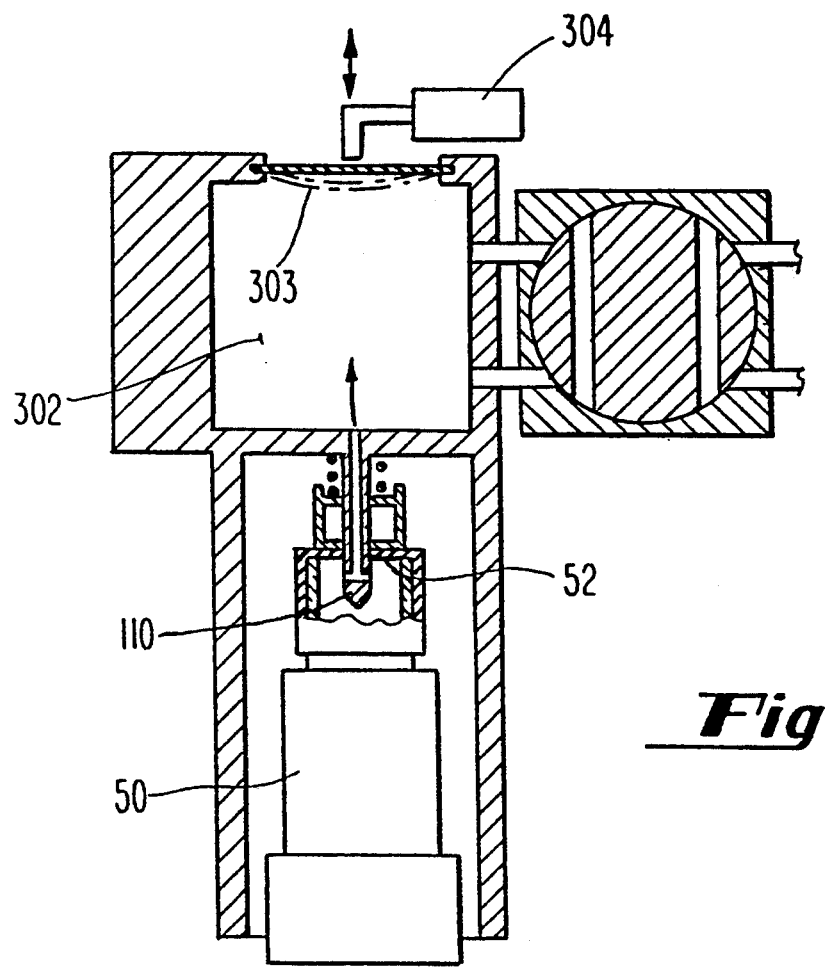
FIG. 4 depicts an alternate embodiment of the external headspace of the present invention that can be agitated to improve uniform dispersion of the gaseous sample.

Further embodiments of the headspace sampling system of the present invention are illustrated in FIGS. 4–5. In the embodiments described above in relation to FIGS. 1–3, the gasses diffused from the sample headspace 52 into the external headspace 102 via the probe 110 that punctured the septum 52 sealing the sample container 50. However, to accelerate the formation of gasses from the sample, the sample can be gently agitated or mixed to provide for example, fresh bulk liquids at the gas/liquid interface. The degree of agitation or mixing used in these embodiments of the present invention is of a lesser degree and kind than that found in the prior art pressurized headspace sampling systems discussed above. In particular, the present invention does not contemplate significantly increasing the pressure within the sample container 50. Agitation in accordance with the present invention can be accomplished, for example, using an ultrasound sonication device that imparts ultrasonic vibrations to the sample container 50. The application of ultrasound to the sample will increase the rate of outgassing of the gaseous components from the sample to the sample headspace 52. This will result in acceleration to equilibrium between the liquid or solid phase of the sample and the gaseous phases since the application of ultrasound increases cavitation inside the sample. As a further advantage, the use of such ultrasonic agitation may in some instances eliminate the need for higher temperatures in the thermally controlled zone 120 discussed above. Those of ordinary skill will be familiar with the methods and apparatus useful for imparting localized ultrasonic vibrations upon the sample container 50.

A further enhancement useful in certain embodiments of the present invention is illustrated in FIG. 4. In these embodiments, the external headspace 302 itself is agitated to accelerate the exchange of gasses between the sample headspace 52 and the external headspace 302. As shown, a variable volume external headspace chamber 302 having a flexible portion 303 is provided. By moving the flexible portion 303 of the external headspace 302 using a vibrator 304, the volume of the external headspace 302 is varied slightly, agitating the gasses in the sample headspace 52. It should be noted, however, that the average volume of the external headspace 302 remains constant, and therefore the advantages of the present invention discussed above with reference to FIGS. 1–3 concerning pressurization would still obtain. As seen in FIG. 5, a stop 56 may be affixed to a portion of the external headspace apparatus 100 for deflecting the septum 54 of the sample container 50. The volume of the sample headspace 52 is varied by moving the sample container relative to the stop 56. As shown in phantom, the septum 54 will be deflected and vary the volume of the sample headspace 52. In either of the embodiments of FIGS. 4–5, the motion imparted to the septum 54 can be a low frequency movement or can be ultrasonically induced.

In any of the above-described embodiments of the present invention, the simple pneumatics associated with the present invention also permit pyrolysis applications. Pyrolysis is similar to headspace sampling, except that the temperature in the temperature controlled zone 120 is on the order of 300 C., as opposed to conventional elevated temperature processes which typically occur at about 100 C.

The present invention also discloses methods of collecting gasses from a sample headspace 52 of a sample contained in a partially filled, sealed sample container, most preferably comprising the steps of inserting a probe 110 through a septum 54 or other means used to seal the sample container and opening a valve 130 to connect the sample headspace 52 to an external headspace 102. Gasses are then permitted to flow from the sample headspace 52 into the external headspace 102. The valve 130 is then closed and a switching valve 104 opened to connect the external headspace 102 to an outlet port 105 to permit the transfer of gasses from the external headspace 102.

In certain embodiments of the methods of the present invention the step of inserting the probe 110 preferably comprises moving the sample container 50 against the probe 110. In other embodiments, the step of opening the valve 130 preferably comprises the step of moving the sample container 50 relative to the probe 110. In certain embodiments of the present invention, the further step of permitting gasses to flow comprises the step of agitating the sample. This step may be accomplished for example, by vibrating the sample container 50 or moving the sample container 50 relative to the probe 110 and against a stop 56, whereby a septum 54 covering the opening of the sample container 50 is deflected. Also, an external headspace 302 may be constructed to comprise a flexible portion 303 wherein the additional step of agitating the sample headspace may be performed by vibrating the flexible portion 303 of the external headspace 302 to increase the rate of gas transfer between the sample and the external headspace. In certain embodiments of the present invention, the step of closing the valve 130 comprises moving the sample container 50 relative to the probe 110. Finally, in certain preferred embodiments of the methods of the present invention, the step of transferring gasses from the external headspace 102 comprises the step of flowing a carrier gas through an inlet port 103 connected to the external headspace 102, whereby the gasses in the external headspace 102 are swept through the outlet port 105.

Although certain embodiments of the present invention have been set forth and discussed above with particularity, these embodiments are exemplary and not meant to limit the scope of the present invention. Upon review of the specification and drawings, those of ordinary skill will immediately realize that numerous modifications, adaptations and variations of the present invention are possible. Accordingly, reference should be made to the appended claims in order to ascertain the scope of the present invention.

What is claimed is:

1. Apparatus for collecting gasses from a sample in a sealed container comprising:
    a substantially constant volume external headspace selectively connectable with the sample container, wherein gas is transferred from the sample container to the external headspace, wherein the external headspace is disposed outside of;
    a first valve means for isolating the external headspace from the sample container; and
    an outlet connecting the external headspace to an analytical instrument, and an inlet connecting the external headspace to a source of carrier gas,
    wherein the gas within the external headspace is transferred to the analytical instrument for further processing by carrier gas flowing into the inlet and through the outlet.

2. The apparatus of claim 1 wherein the means for isolating the external headspace comprises a first valve disposed between the container and the external headspace.

3. The apparatus of claim 2, wherein the first valve is a shuttle valve adapted to engage a portion of the sample container and is operated by the relative motion of the sample container.

4. The apparatus of claim 3 wherein the probe has a longitudinal axis and the shuttle valve is disposed coaxially with the longitudinal axis and is operated by being displaced along the longitudinal axis.

5. The apparatus of claim 1, further comprising a second valve disposed between the outlet and an inlet to the analytical instrument.

6. The apparatus of claim 5, wherein the analytical instrument comprises a gas chromatograph.

7. The apparatus of claim 5, wherein the second valve is a switching valve connected to a source of carrier gas, whereby carrier gas can selectively flow through the inlet port and sweep gases in the external headspace through the outlet port.

8. The apparatus of claim 1, further comprising a probe for selectively connecting the external headspace to the sample container, the probe comprising a tubular portion having a hollow axial portion extending from a proximal end connected to the external headspace toward a closed distal end, the hollow axial portion intersecting a side passage disposed substantially perpendicular to the hollow axial portion, the side passage permitting gas flow into the hollow axial portion.

9. The apparatus of claim 7 wherein the external headspace is described by an arcuate hollow portion describing a curve extending between the inlet port and the outlet port, the arcuate portion being connected to the probe whereby gases can flow through the probe into the external headspace, and the arcuate portion provides a curved flow path for gases flowing between the inlet and the outlet.

10. The apparatus of claim 1, further comprising an ultrasonic vibrator for inducing localized ultrasonic vibrations in the sample container, whereby the rate of outgassing of the sample is increased.

11. The apparatus of claim 10, further comprising stop that is urged against the sample container; and vibrator means for inducing vibration between the sample container and the stop.

12. The apparatus of claim 1, wherein at least a portion of the external headspace is flexible, and further comprises vibrator means for vibrating the flexible portion, whereby the dispersion of sample gasses between the sample headspace and the external headspace is accelerated.

13. The apparatus of claim 1, further comprising means for creating one or more temperature controlled zones within the apparatus.

14. The apparatus of claim 1, wherein the sample container is sealed by a septum.

15. The apparatus of claim 14, wherein the means for transferring the external headspace contents for further processing comprises a probe insertable through the septum in a sealed manner.

16. A method of collecting the gasses from the sample headspace of a sample contained in a sample container comprising the steps of:

selectively connecting a substantially constant volume external headspace with the sample container;

permitting gasses in the sample container to flow into the external headspace;

isolating the external headspace from the sample container by operating the valve separate from the external headspace; and transferring gasses from the external headspace by flowing a carrier gas through the external headspace.

17. The method of claim 16, wherein the step of selectively connecting the external headspace comprises the steps of:

inserting a probe through the septum;

opening a shuttle valve to connect the sample headspace to an external headspace.

18. The method of claim 17 wherein the steps of isolating the external headspace from the sample container and transferring gasses from the external headspace comprise the steps of:

closing the shuttle valve;

opening a switching valve to connect the external headspace to an outlet port.

19. The method of claim 16, further comprising the step of agitating the sample headspace.

20. The method of claim 19, wherein the sample container is sealed by a septum and the step of selectively connecting the external headspace comprises inserting a probe through the septum, and wherein the step of agitating the sample headspace comprises the step of moving the sample container relative to the probe, whereby the septum is deflected.

21. The method of claim 19, wherein the external headspace comprises a flexible portion, and further comprising the step of agitating the sample headspace by vibrating the flexible portion of the external headspace.

22. The method of claim 16, wherein the step of flowing a carrier gas through the external headspace comprises the step of opening an inlet port and an outlet port connected to the external headspace, whereby the gasses in the external headspace are swept from the headspace through the outlet port by the carrier gas.

23. Apparatus for collecting gases from a sample container comprising:

an external headspace having a first port connecting the sample container to the external headspace via a probe and a second port for connecting the sample headspace to means for further processing gasses;

a shuttle valve for controlling the flow of gasses through the probe; and a second valve for controlling the transfer of the gasses from within the external headspace through the second port.

24. The apparatus of claim 23, wherein the sample container is sealed by a septum and wherein the probe is adapted to be inserted through the septum in a sealed manner, whereby the sample container urges against the shuttle valve during insertion to control gas flow.

* * * * *